United States Patent
Worthington et al.

(10) Patent No.: US 7,088,650 B1
(45) Date of Patent: Aug. 8, 2006

(54) METHODS AND APPARATUS FOR OPTICAL DISC DATA ACQUISITION USING PHYSICAL SYNCHRONIZATION MARKERS

(76) Inventors: Mark O. Worthington, 13841 Tustin East #138, Tustin, CA (US) 92780; Gregory R. Basile, 2918 Maydelle, Farmers Branch, TX (US) 75234; James R. Norton, 19321 Fisher La., Santa Ana, CA (US) 92705

( * ) Notice: Subject to any disclaimer, the term of this patent is extended or adjusted under 35 U.S.C. 154(b) by 0 days.

(21) Appl. No.: 09/643,106

(22) Filed: Aug. 21, 2000

Related U.S. Application Data

(60) Provisional application No. 60/150,288, filed on Aug. 23, 1999.

(51) Int. Cl.
*G11B 15/52* (2006.01)

(52) U.S. Cl. .............. 369/47.15; 369/47.47; 369/291; 369/47.48; 359/368; 250/234

(58) Field of Classification Search .............. 369/275.3, 369/47.15, 52.1, 53.21, 84, 111, 272, 275.1, 369/273, 277, 44.29, 124.08, 47.31, 53.2, 369/47.48, 59.26, 47.47, 291; 428/64.1; 359/368, 359/383; 250/234, 216, 208.1; 356/73; 422/82.05, 422/82.09

See application file for complete search history.

(56) References Cited

U.S. PATENT DOCUMENTS

| | | | | |
|---|---|---|---|---|
| 4,870,508 A | * | 9/1989 | Van Rosmalen et al. | 369/275.1 |
| 5,532,874 A | * | 7/1996 | Stein | 359/368 |
| 5,538,773 A | * | 7/1996 | Kondo | 369/275.1 |
| 5,545,540 A | | 8/1996 | Mian | 435/91.2 |
| 5,686,271 A | | 11/1997 | Mian et al. | 435/91.1 |
| 5,717,519 A | * | 2/1998 | Sugiyama et al. | 359/368 |
| 5,761,165 A | * | 6/1998 | Takeda et al. | 369/47.31 |
| 5,781,526 A | * | 7/1998 | Nishizawa et al. | 369/275.3 |
| 5,892,577 A | | 4/1999 | Gordon | 356/73 |
| 5,922,617 A | | 7/1999 | Wang et al. | 436/518 |
| 6,030,581 A | | 2/2000 | Virtanen | 422/68.1 |
| 6,063,589 A | | 5/2000 | Kellogg et al. | 435/24 |
| 6,104,686 A | * | 8/2000 | Whitcher et al. | 369/111 |
| 6,121,048 A | | 9/2000 | Zaffaroni et al. | 436/45 |
| 6,190,748 B1 | * | 2/2001 | Xavier et al. | 369/275.1 |
| 6,195,325 B1 | * | 2/2001 | Okanishi | 369/124.08 |
| 6,226,109 B1 | * | 5/2001 | Tompkin et al. | 369/275.1 |
| 6,292,318 B1 | * | 9/2001 | Hayashi | 369/44.29 |
| 6,399,936 B1 | * | 6/2002 | Hang et al. | 250/216 |
| 6,545,265 B1 | * | 4/2003 | Czarnetzki et al. | 250/234 |

FOREIGN PATENT DOCUMENTS

| | | |
|---|---|---|
| EP | 0 417 305 A1 | 3/1991 |
| EP | 0 702 728 B1 | 4/1998 |
| WO | WO 97/21090 | 6/1997 |
| WO | WO 98/07019 | 2/1998 |
| WO | WO 98/12559 | 3/1998 |
| WO | WO 98/28623 | 7/1998 |

\* cited by examiner

*Primary Examiner*—Tan Dinh
*Assistant Examiner*—Kim-Kwok Chu

(57) ABSTRACT

Methods and apparatus for using physical synchronization markers during optical disc data acquisition are provided. In accordance with this invention, physical synchronization markers on optical discs and/or disc covers can be used to determine absolute and/or relative positions on the disc or cover and control data acquisition. A method for acquiring data includes detecting at least one physical synchronization marker and reading data in response to detecting the marker.

5 Claims, 12 Drawing Sheets

METHODS AND APPARATUS FOR OPTICAL DISC DATA ACQUISITION USING PHYSICAL SYNCHRONIZATION MARKERS

This application claims the benefit of Provisional Application Ser. No. 60/150,228 filed Aug. 23, 1999.

BACKGROUND OF THE INVENTION

1. Field of the Invention

The present invention relates generally to physical markers located on optical discs. More particularly, the present invention is directed to using physical markers to provide synchronization during acquisition of data from optical discs.

2. Description of Related Art

Recent developments in optical disc design, optical disc manufacture, and in the design and manufacture of drives for reading these discs have now made it possible to use optical disc drives to interrogate disc surfaces for the presence of nonoperational structures.

As described more fully in copending and commonly owned U.S. patent application Ser. No. 09/183,842 filed Oct. 30, 1998, 09/311,329 filed May 14, 1999, and 60/134,368 filed May 14, 1999, hereby incorporated by reference in their entireties, these nonoperational structures produce signals during trackable reading that are discriminably embedded within the normal electrical responses; the embedded signals report physical properties of the nonoperational structures. In conjunction with analysis software newly developed for this purpose and described more fully in "Methods And Apparatus For Analyzing Nonoperational Data Acquired From Optical Discs," Worthington et al., U.S. patent application Ser. No. 09/378,878 filed on Aug. 23, 1999, hereby incorporated herein by reference in its entirety, permits these signals to be characterized, classified, mapped, and represented visually.

In essence, these developments permit the disc drive to be used for scanning confocal laser microscopic inspection of one or more disc surfaces.

The robustness of this approach makes possible the optical inspection of structures having enormous variety in shape, size, and chemical and optical properties. This flexibility in turn permits such nonoperational structures to be used for a wide variety of signaling chores. For example, as described more fully in copending and commonly owned U.S. patent application Ser. No. 08/888,935 filed Jul. 7, 1997 and 09/120,049 filed Jul. 21, 1998, hereby incorporated by reference to their entireties, such nonoperational structures can be used to signal the results of chemical and biological assays, ranging from immunoassay, to enzymatic assays, to nucleic acid hybridization assays, to direct detection of mammalian cells.

In each of the laser microscopic applications of optical disc drives, though, the nonoperational signaling structures must be disposed upon or near a surface of the optical disc prior to reading. For some applications, it may suffice to dispose the nonoperational structures randomly upon the disc surface, as in certain simple counting applications. For other applications, such as in nucleic acid array analysis (see, e.g., WO 98/12559), it may instead be preferable to dispose these nonoperational signaling structures in one or more ordered arrays. In order to detect these structures, there exists a need in the art or methods, apparatus, and compositions that facilitate the acquisition of data from the optical disc.

SUMMARY OF THE INVENTION

The present invention involves methods and apparatus for using physical synchronization markers during optical disc data acquisition. In accordance with this invention, physical synchronization markers on optical discs and/or disc covers can be used to determine absolute and/or relative positions on the disc or cover and control data acquisition. A method for acquiring data includes detecting at least one physical synchronization marker and reading data in response to detecting the marker.

BRIEF DESCRIPTION OF THE DRAWINGS

Objects and advantages of the invention will be apparent upon consideration of the following detailed description, taken in conjunction with the accompanying drawings, in which the reference characters refer to like parts throughout, and in which.

DETAILED DESCRIPTION OF THE INVENTION

In order that the invention herein described may be fully understood, the following detailed description is set forth. In the description, the following terms are employed.

As used herein, the term "radial" denotes, in the plane of one or more of a disc's data-encoding surfaces, the direction forward or backward along a tracking spiral. A disc surface, according to this invention, can be an internal or external surface.

As used herein, the term "tangential" denotes, in the plane of one or more of a disc's data-encoding surfaces, the direction inward or outward along a line drawn from the disc's physical center to its outer circumference.

As used herein, the term "turn" denotes a 360° segment of a spiral track of an optical disc.

As used herein, the term "index" denotes a physical structure, which can be nonoperational or operational, on or in the optical disc.

Physical synchronization markers are useful for reducing the amount of data for a predetermined period of time after detection of the marker during disc rotation. Alternatively, physical synchronization markers can be used to reduce the amount of data the optical disc reader reads by only acquiring data for a period of time that begins after detection of a first marker during disc rotation and that ends after detection of a second marker. Thus, it will be appreciated that more than one physical synchronization marker can be used on a single disc.

Figure 10:
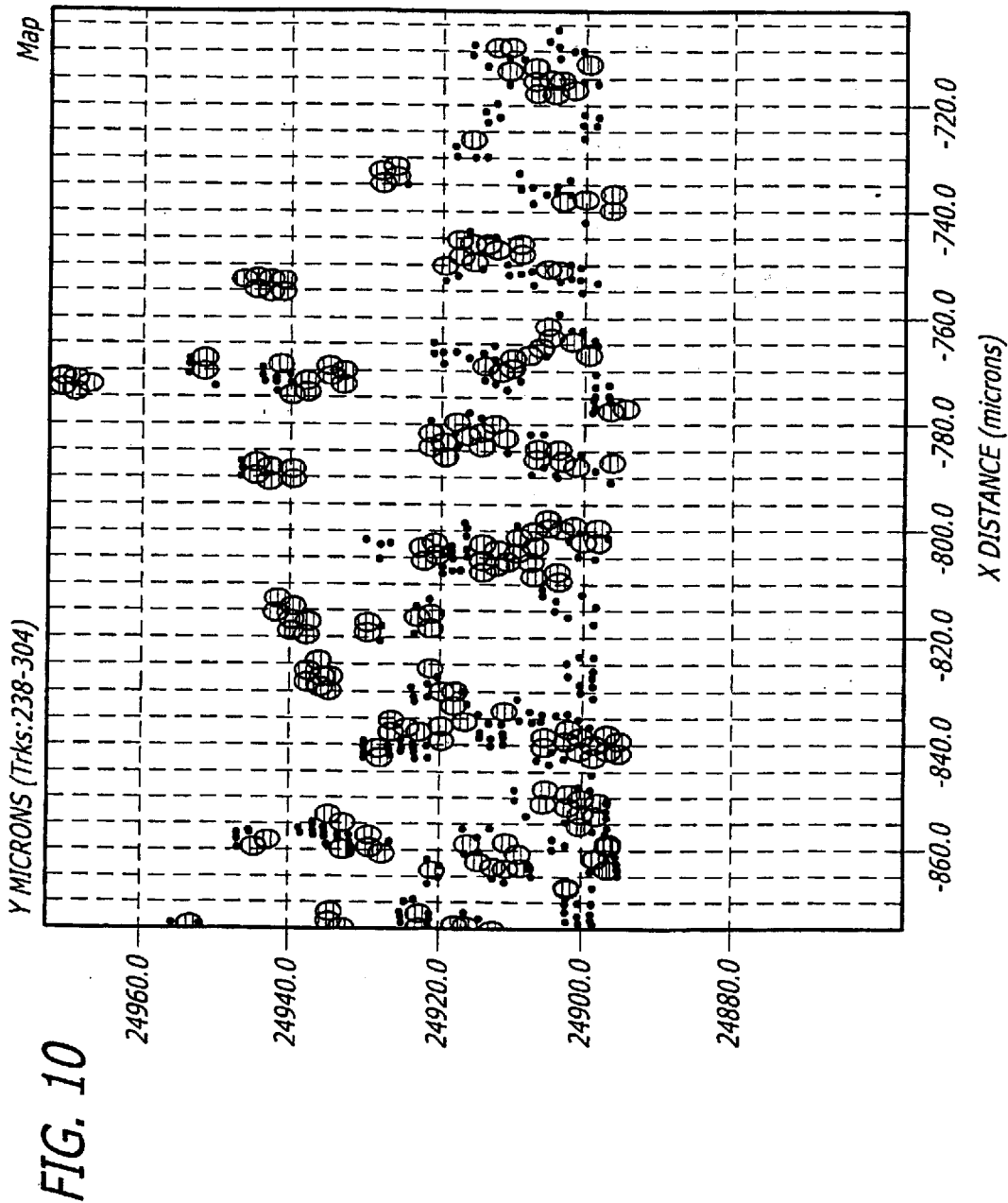
FIG. 10 presenting, in X axis registration with FIG. 9, a computer-generated reconstruction mapping with icons the location of the detected spheres.
Figure 11:
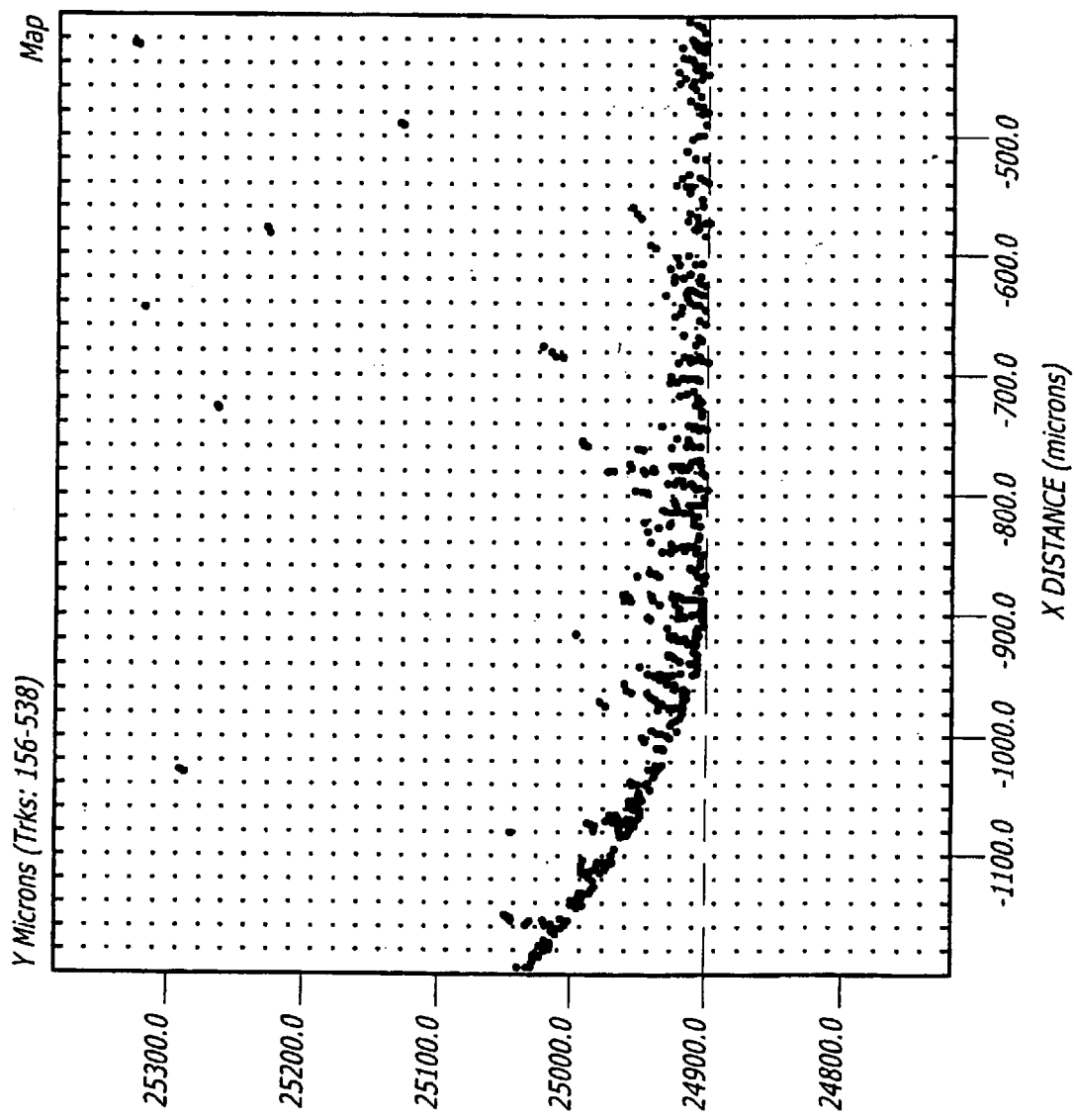
FIG. 11 shows a computer-generated two-dimensional representation of the same disc shown optically in FIGS. 4 and 5, and electrically in FIGS. 6–10, with both X axis and Y axis adjusted to present lesser magnification.
Figure 12:
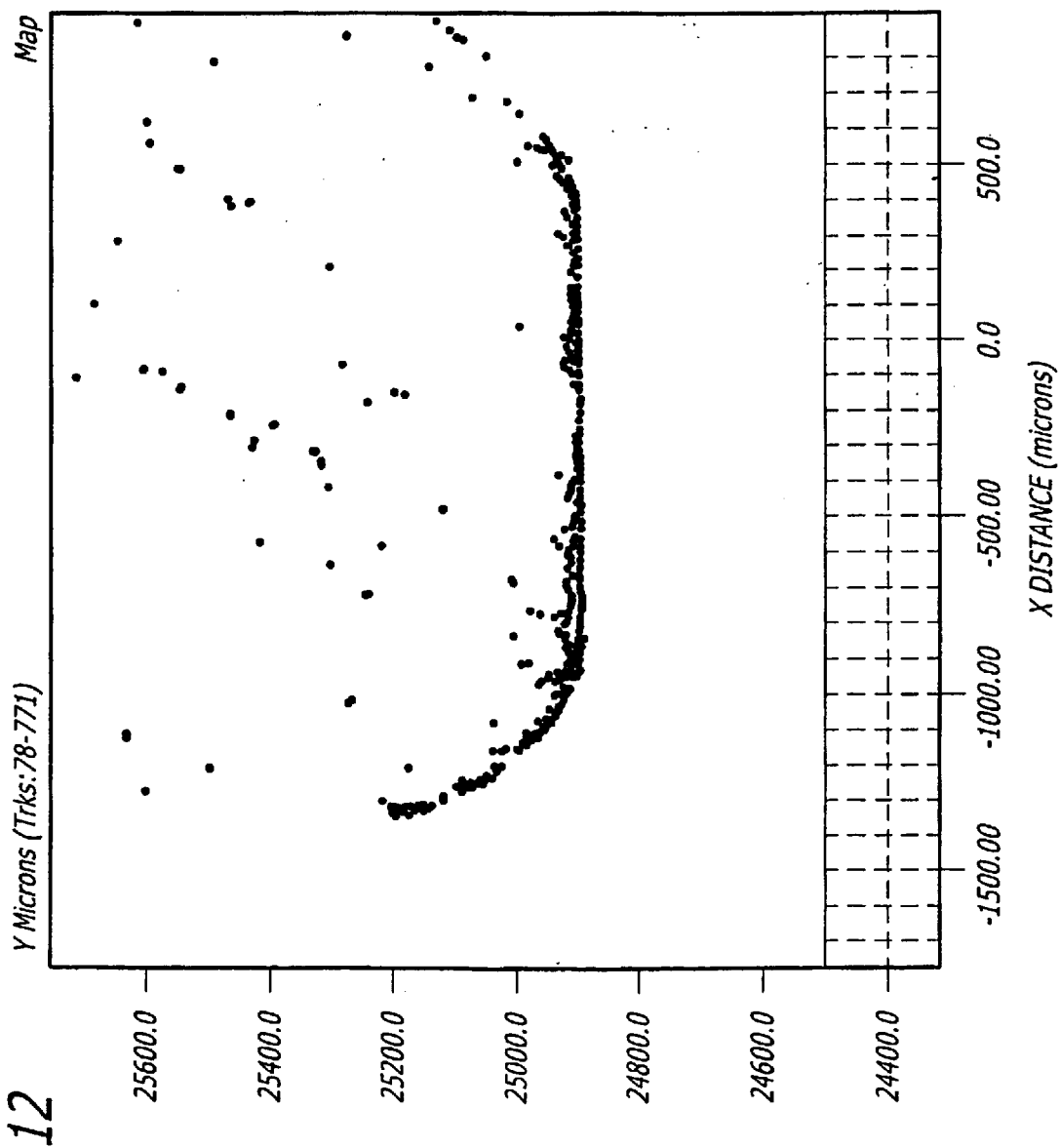
FIG. 12 shows a computer-generated two-dimensional representation of the same disc shown optically in FIGS. 4 and 5 and electrically in FIGS. 6–10, with X axis and Y axis further adjusted to present lesser magnification.
Figure 13:
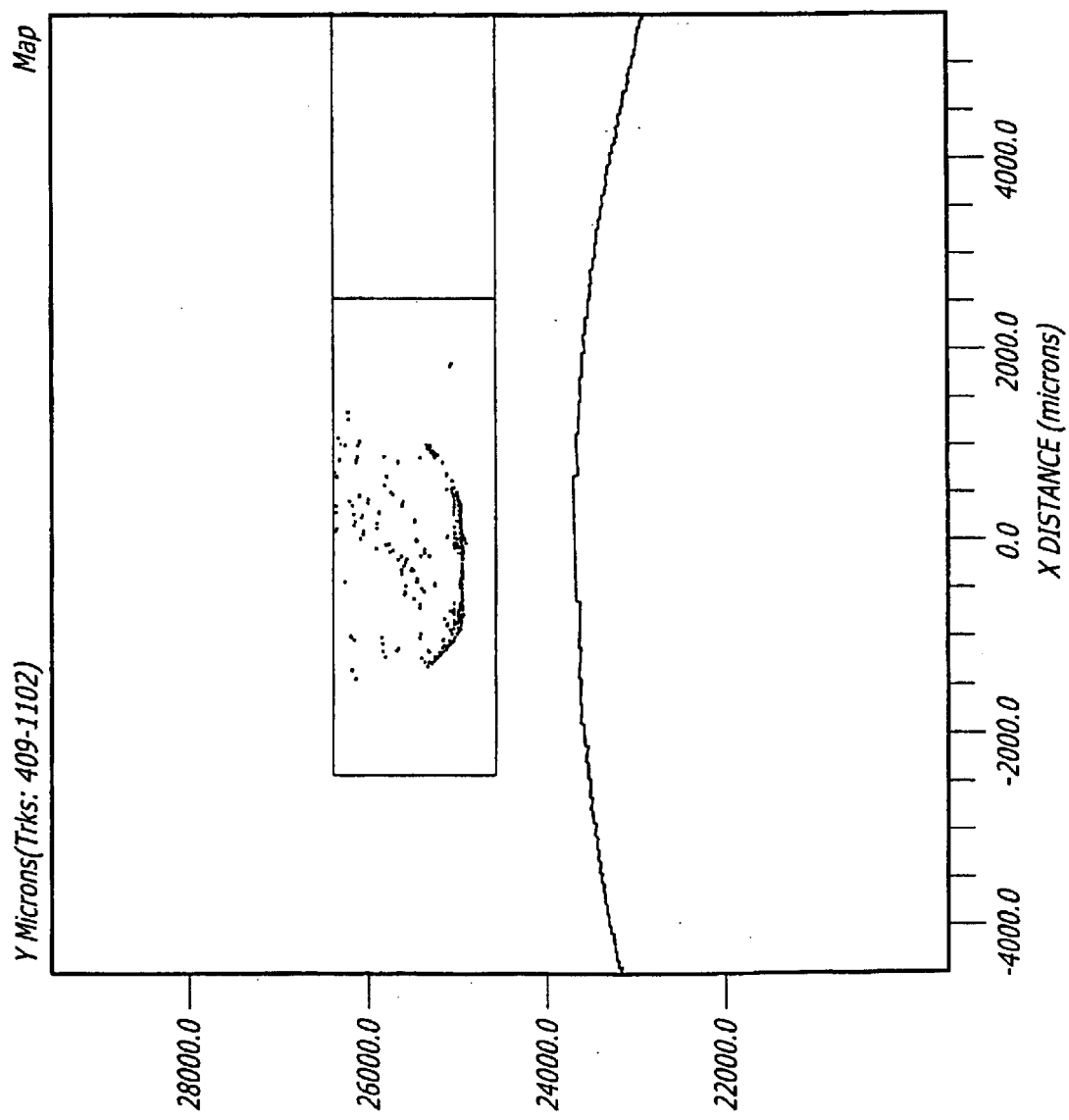
FIG. 13 shows a computer-generated two-dimensional representation of the same data, with the acquired digital data, shown boxed, mapped to a representation of a disc.
Figure 14:
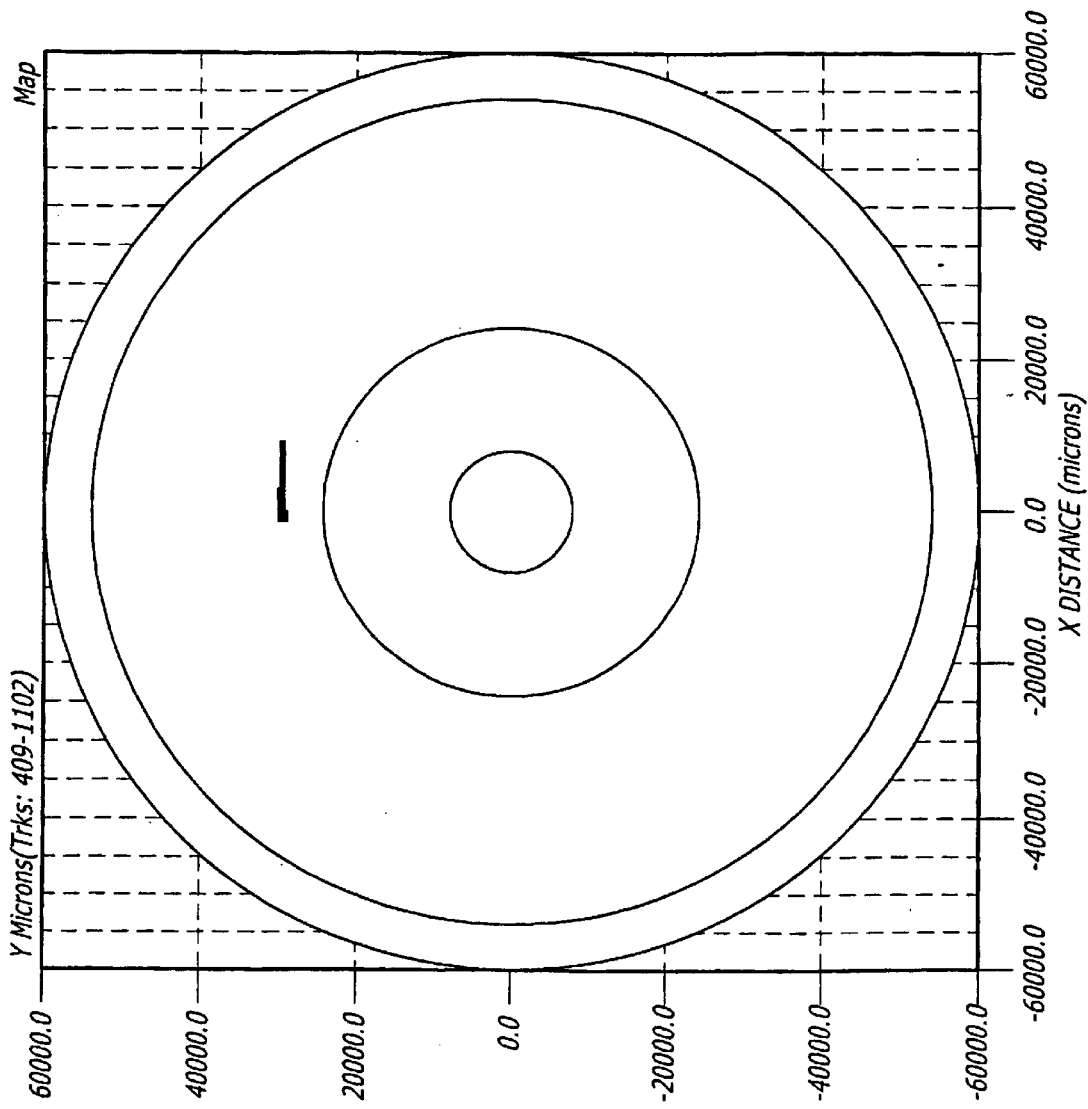
FIG. 14 reducing further the apparent magnification, shows the location of the detected area on a representation of a disc.

Moreover, physical synchronization markers can be used to embed absolute and/or relative position markers in the data when the physical synchronization markers are detected by an optical pickup. Then, by aligning the embedded position markers, the data can be more accurately mapped onto a representation of a disc, as shown, for example, in FIG. 10.

Figure 1A:
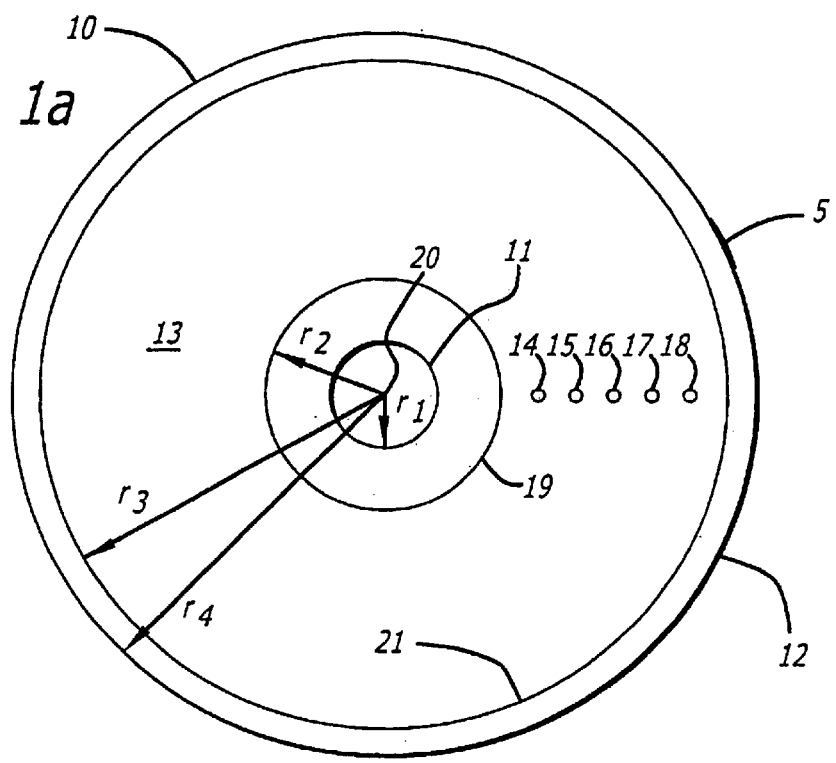
FIG. 1a shows a simplified representation of a CD-R optical disc with a physical synchronization marker and five sample areas according to this invention.
Figure 1B:
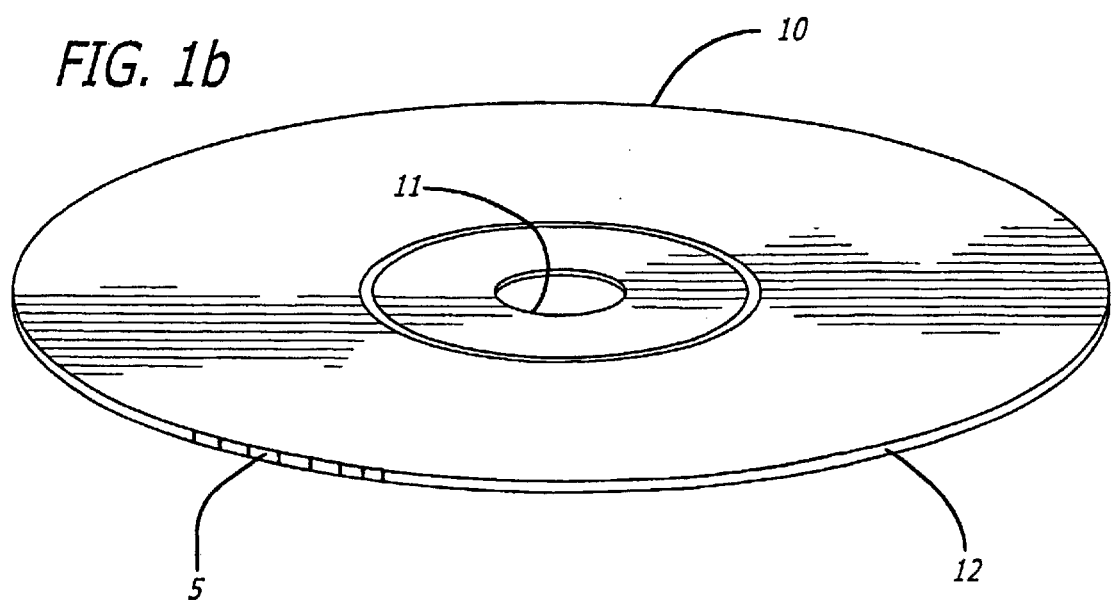
FIG. 1b is a top perspective view of the optical disc shown in FIG. 1a, showing in particular the location of the physical synchronization marker, which is disposed on the optical disc's edge, according to this invention.

Physical synchronization markers can be provided to an optical disc in any way, as long as the marker can be detected by a sensor during disc rotation and does not substantially degrade operation of the optical disc drive. For example, a physical synchronization marker can be provided on an optical disc by applying a small amount of correction fluid at or near the edge of the disc (or cover, as described below). As shown in FIGS. 1a–1b and described in the Example herein, marker 5 is placed on the edge of the disc. It will be appreciated, however, that such a marker could be placed at any convenient location of the disc, including area 13 of disc 10 shown in FIG. 1a. One type of correction fluid that has been used according to this invention is sold under item no. 564-01 under the trademark Liquid Paper®, available from the Stationery Products Division of The Gillette Company, of Boston, Mass.). Alternatively, as shown in FIGS. 2–4, an excimer laser can be used to accurately and reproducibly mark (e.g., by ablating, melting, etc.) a disc at one or more locations.

In yet another alternative, one or more pits and/or lands could be used as physical synchronization markers. The use of pits and/or lands as physical synchronization markers is different from their use as logical markers because physical synchronization markers need not be decoded; the physical markers need only be detected. Additional logical synchronization information, however, could be encoded on the disc along with physical synchronization markers.

FIG. 1 shows the relative placement of various physical features, including a physical synchronization marker and five sample areas, of optical disc 10. Before discussing these placements, however, a brief discussion of the physical dimensions of disc 10 is appropriate.

The nominal thickness of disc 10 is about 1.2 mm, however, the senior standard for compact disk technology (colloquially, the "Red Book"), republished as IEC 908, permits physical thickness of 1.1–1.5 mm (for all layers combined). Readers are capable of accommodating some additional variance, however, and discs suitable for reading by CD and DVD drives may have a depth maximally of about 2.4 mm and minimally of about 0.8 mm, preferably 1.0–1.4 mm, more preferably 1.1–1.3 mm, most preferably 1.2 mm. The nominal outer diameter of an optical disc according to this invention is about 120 mm, but disk readers may accommodate disks of radial diameter of 100–140 mm, preferably 100–130 mm, more preferably 115–125 mm, and most preferably 120 mm.

The standard also provides for discs with radial diameter of 8 cm (80 cm): the dimensions of the mounting and clamping rings remain the same as that for 120 mm discs, as does disc depth; only the outer diameter is reduced, reducing the data area of the disc. Commercially available CD and DVD readers and reader/writers accommodate discs of this diameter in their disc tray. Such discs present certain advantages in the practice of the present invention, among which are a commensurate reduction in assay sample volume required to effect contact with the entire disc surface, as well as the ability to package such disc in a sleeve dimensioned identically to the sleeve of a 3 ½ magnetic floppy disc.

Furthermore, various additional standards, such as those defining a (magneto-optical) mini disc or analogue laser disc have been, or will be, devleoped. Thus, the discs of the present invention may have a radial diameter as small as 50 mm and as large as that for a standard laser disc, and may be adapted to such size standards as are developed in the future. One skilled in the art would further recognize that the term "disc" contemplates any suitably rotatable media, whether or not perfectly circular.

Returning to FIGS. 1a–1b, edges 11 and 12 represent the inner and outer diameters of optical disc 10. Area 13 represents the area of disc 10 that is trackable using the wobble of a CD-R disc. In the case of the embodiment shown in FIG. 1a, the radius $r_1$ of the center hole is 7.5 mm. The wobble track starts at radius $r_2$ (e.g., about 21.7 mm in the tangential direction as measured from center point 20) and ends at radius $r_3$ (e.g., about 58.7 mm in the tangential direction as measured from center point 20). Outside edge 12 at radius $r_4$ (e.g., about 60.0 mm in the tangential direction as measured from center point 20). Sample areas 14–18 represent areas of interest that can be read, mapped, and analyzed, as described in commonly owned Worthington et al. U.S. patent application Ser. No. 09/378,878, filed Aug. 23, 1999, entitled Methods And Apparatus For Analyzing Operational and Nonoperational Data Acquired From Optical Discs, and which is incorporated by reference herein in its entirety. As shown in FIG. 1b, physical synchronization marker 5 is shown on edge 12 of disc 10.

Tangential position and A-time can be related by the following approximation:

$$\text{A-time} = \frac{\pi(R_o^2 - R_i^2)}{\text{pitch} * v},$$

where A-time has units of seconds, $R_o^2$ is the current tangential position, in units of mm, as measured from the center of the disc $R_i^2$ is the inner radius of A-time (which is about 24.8 mm, defined to be 00:00, in units of minutes:seconds), as measured from the center of the disc, pitch is the track pitch in microns, and v is the linear velocity, in units of meters per second.

Thus, an approximate tangential position of a sample area can be determined by reading an A-time decoded from the wobble track. As used herein, the A-time is an amount of time that corresponds to the length of the track from the beginning of the disc. The following table lists the five sample areas, their respective A-times, and their approximate tangential positions:

| Sample Area | A-time (minutes:seconds) | Corresponding tangential positions (mm) |
| --- | --- | --- |
| 14 | 8:19 | 30.3 |
| 15 | 18:18 | 35.9 |
| 16 | 29:57 | 41.4 |
| 17 | 43:17 | 46.9 |
| 18 | 58:16 | 52.5 |

The approximate tangential positions listed above were calculated adding integral multiples of 5.53 mm to the innermost diameter of the wobbled track region. 5.53 mm was calculated by dividing the approximate tangential distance on which the wobbled track is disposed (58 mm−24.8 mm=33.2 mm) by the number of sample areas (i.e., 5) plus 1 (i.e., 6).

In addition to an A-time, an a-period and b-period can be used for controlling data acquisition. As used herein, the term "a-period" is a user-defined delay after receipt of a triggering signal, which is generated by a physical synchronization marker. Also, the term "b-period" is an amount of time in which data is acquired. Thus, these terms can be used to control data acquisition when combined with a physical synchronization marker; acquisition can be for a user-specified duration following a user-defined delay.

This invention provides a method for determining the physical location, absolute and/or relative, of structures on an optical disc (e.g., for mapping). It will be appreciated that the use of the term "absolute" location as used herein, only refers to an approximate absolute position, the accuracy of which depends on a number of factors. The primary means of determining the tangential and/or radial position of a structure is to physically mark the disc with a physical synchronization marker at a known location. An external sensor mounted in the drive or the objective assembly can detect the physical synchronization marker. Alternatively, the objective assembly, which is designed to read data from the optical disc, can also be used to detect the location of the marker. A position marker, which corresponds to a physical synchronization marker, is preferably embedded synchronously with the data derived from the sampled signal.

By knowing the position of the physical synchronization marker and counting the number of data points (i.e., samples) since the physical synchronization marker was detected, the radial position of the data point can be estimated. One way that this estimate can be made is by keeping track of the number of times the physical synchronization marker was detected for a relative tangential position and reading the A-time of the wobble track for an estimate of the absolute position.

Absolute tangential position may also be estimated by measuring the period of time between detecting two physical synchronization markers. This estimation is possible because the drive spins at a controlled speed. For example, speed can be controlled using a constant linear velocity ("CLV") mode or a constant angular velocity ("CAV") mode. Although both modes can be used in accordance with this invention, CLV mode has been successfully tested and used (see Example). In CLV mode, the disc typically spins at a constant linear velocity of about 1.2 meters per second, although this velocity can be changed. A constant linear velocity necessarily means a varying angular velocity as the objective assembly moves tangentially outward. In other words, the number of revolutions of the disc per second depends on the absolute tangential position of the objective assembly (e.g., read head). This number can be derived by measuring the time elapsed between two successive detections of the physical synchronization marker. The following equation is used to determine the angular velocity a, which is measured in revolutions per second (rps):

$$\omega = \frac{1}{t_{n+1} - t_n}$$

where $t_n$ is the time at which the marker was measured and $t_{n+1}$ is the next time at which the marker was measured.

The absolute tangential position can therefore be determined according to the following equation:

$$D = \frac{1.2 \text{ (m/s)}}{(2\omega\pi)}$$

wherein D is the tangential distance from the center of the disc and ω is the angular velocity in revolutions per second.

A more accurate estimate of the radial position on the disc can be made by synchronizing the sample clocking with the clock embedded in the wobble track. This can be accomplished by using a phased lock loop to multiply the 22.05 kHz clock embedded in the wobble track signal to the appropriate sampling rate. A sampling rate of about 12 MHZ has been demonstrated successfully.

Figure 2A:
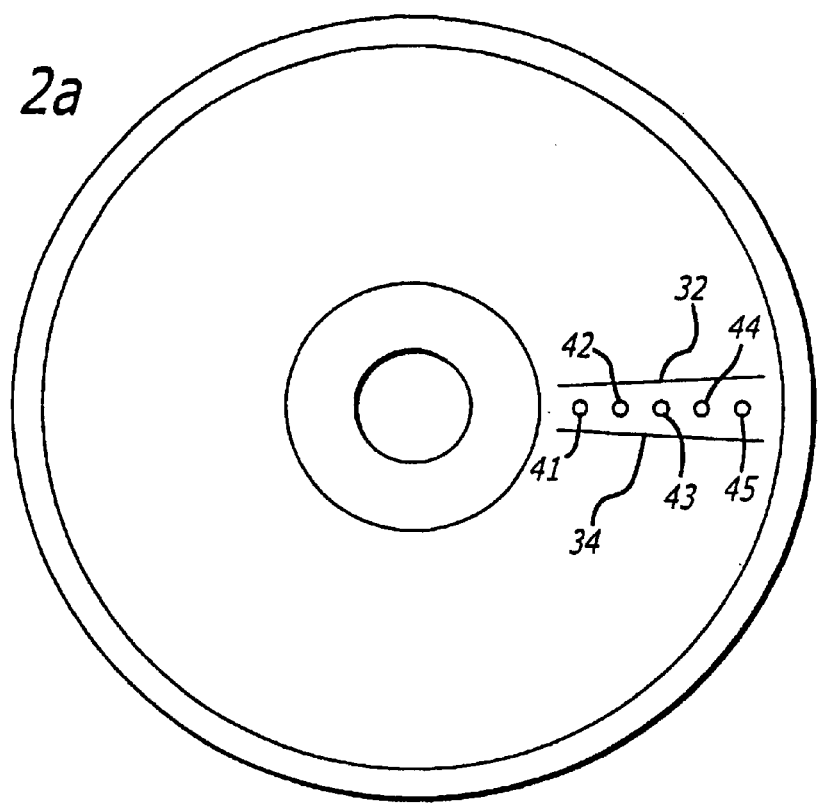
FIG. 2a shows a simplified representation of a further CD-R optical disc with five sample areas and two physical synchronization markers, one of the markers being rotationally earlier and one of the markers being rotationally later than the sample areas, according to this invention.
Figure 2B:
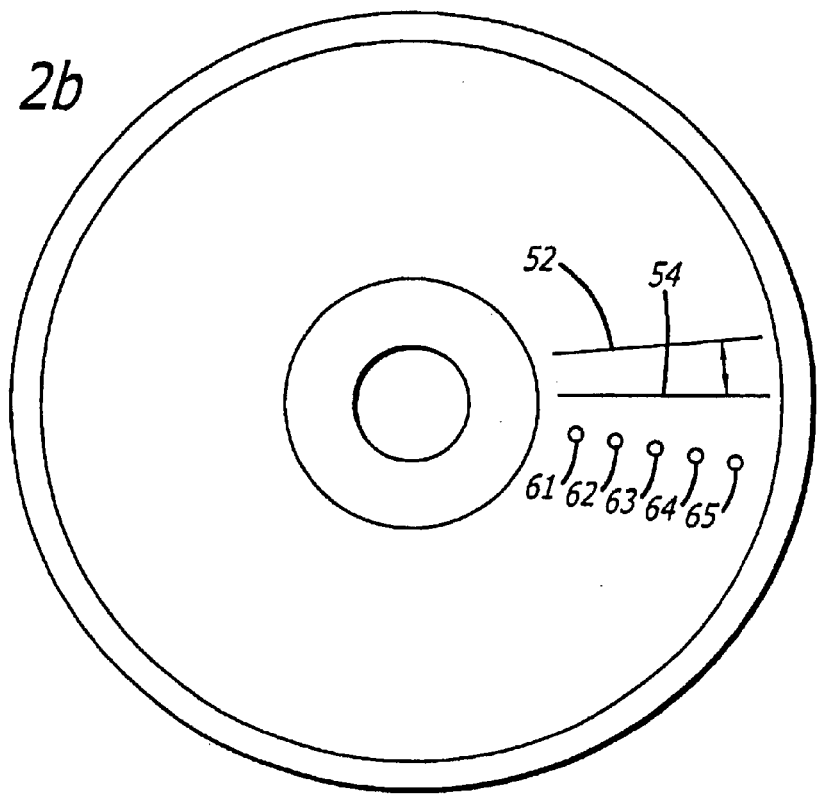
FIG. 2b shows a simplified representation of another CD-R optical disc with five sample areas and two physical synchronization markers rotationally earlier than the sample areas according to this invention.
Figure 3A:
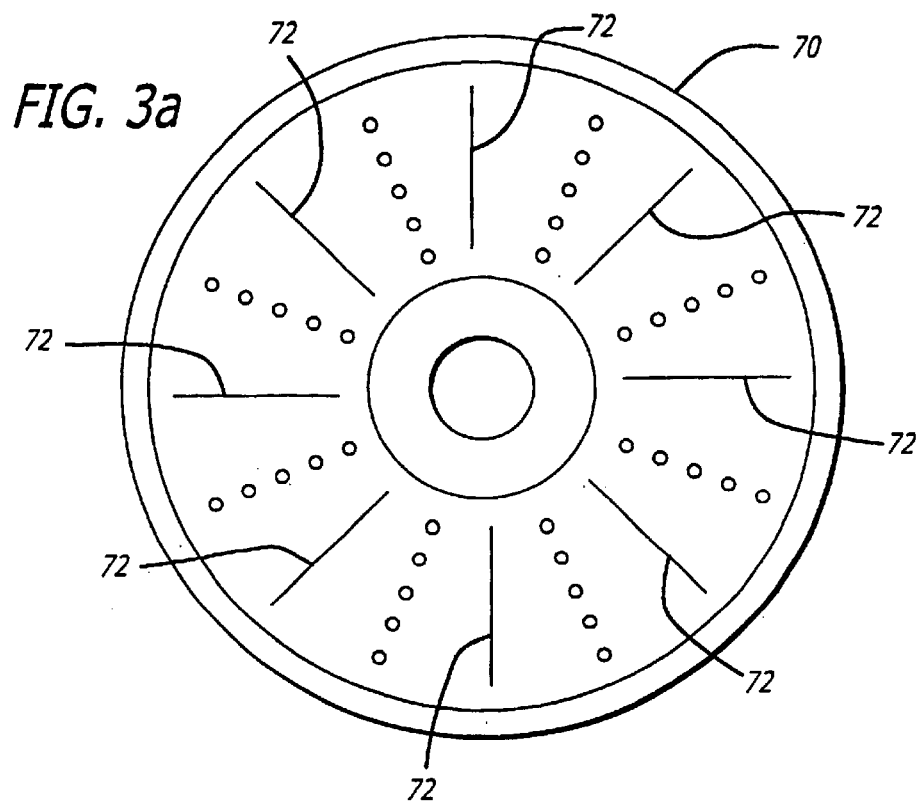
FIG. 3a shows a simplified representation of yet another CD-R optical disc with eight physical synchronization marker and twenty-four sample areas according to this invention.
Figure 4:
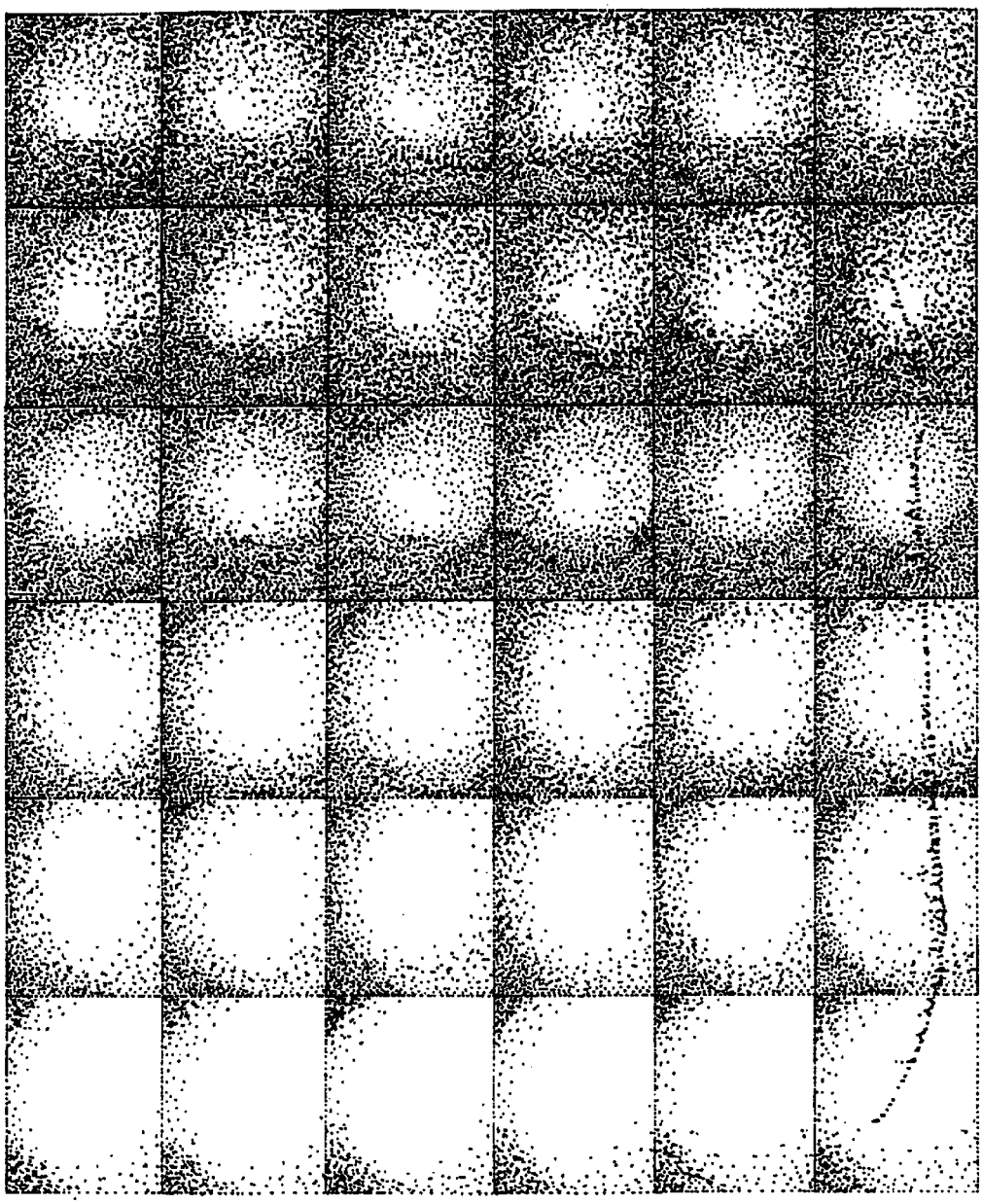
FIG. 4 shows a two-dimensional composite of light microscopic images acquired at 300 × magnification of the laser proximal surface of an optical disc with 2.8 μm spheres adherent to a metalized surface and aligned substantially along a track.

As shown in FIGS. 2a, 2b, and 3a, the number of markers used on a single disc can vary. FIG. 2a, for example, shows a simplified representation of a CD-R optical disc with two physical synchronization markers and five sample areas according to this invention. Physical synchronization markers 32 and 34 can be used with a single sample area (not shown) or array of sample areas 41–45. In this way, marker 32 can be used to initiate data acquisition and marker 34 can be used to terminate data acquisition. Thus, first marker 32 can be a tangentially oriented line at a location rotationally earlier than the sample area(s) (e.g., assay sites) and second marker 34 can be another tangentially oriented line at a location rotationally later than the sample area(s). It will be appreciated that if the direction of rotation can change, then the terms "rotationally earlier" and "rotationally later," as used herein, would refer to one of the rotational directions.

Alternatively, two or more markers can be placed on the same side of a sample area. FIG. 2b, for example, shows markers 52 and 54, both of which are tangentially oriented lines at a location rotationally earlier than the sample area(s). If the distance between markers 52 and 54 varies tangentially and is known, then that distance, which can be calculated by multiplying the period of time measured along a particular track by the rotational speed (see below), can be used to calculate the absolute tangential position on the disc. This position, in turn, can also be used to report information regarding a sample area number or size, if the relationship to the position is previously stored. For example, if it is known that the area of sample area 61 is radially shorter than sample area 65, a determination of an absolute tangential position could be used to control the period of time for acquiring data. Thus, the physical synchronization markers can be used to control the start and stop of data acquisition, as well as to determine the tangential position of the track being read.

Furthermore, it will be appreciated that the shape and orientation of the markers can vary. In other words, the markers need not be straight lines nor need they be tangentially oriented. For example, types of physical synchronization markers that could be used according to this invention include circles and boxes that surround sample areas.

FIGS. 3a shows another way that multiple synchronization markers can be used on a single disc. Here, another CD-R optical disc 70 includes eight physical synchronization markers 72 and twenty-four sample areas (three circular samples areas between each pair of adjacent markers 72). Although disc 70 only includes twenty-four sample areas, any number of areas could be included. And, because the area required to perform an assay according to this invention is so small, a very large number of sample areas can be used on a single surface of a disc, including one thousand or more.

In order to detect a physical synchronization marker, a disc drive can be modified by mounting a sensor that looks at a position on the disc where the physical synchronization marker is located. Thus, according to the embodiment shown in FIGS. 1a–1b, the sensor can be mounted in the drive where edge 12 of disc 10 passes during rotation. Alternatively, the sensor can be mounted in the drive where edge of disc 10 passes during rotation. Thus, the sensor is in a known position relative to the read head of the drive. During operation, the sensor can detect marker 5 by monitoring changes in the level of reflected light. This can be done by shining a light on the edge of the disc and receiving light reflected by marker 5 with a photodiode. Thus, when marker 5 is not under the sensor, no light is reflected by the marker and the sensor indicates its absence. And, when marker 5 is under the sensor, light is reflected by marker 5 and the sensor indicates its presence.

It will be appreciated that in an alternative embodiment, marker detection can be effected by monitoring changes in the level of light transmitted through, rather than reflected by, the disc. It will also be appreciated that detection of the physical maker need not be based solely on passive reflectance or transmittance, but may utilize any other optically detecable signal element that can be detected with each rotation of the disc, including, for example, fluorescent and phosphorescent signal elements.

Figure 3B:
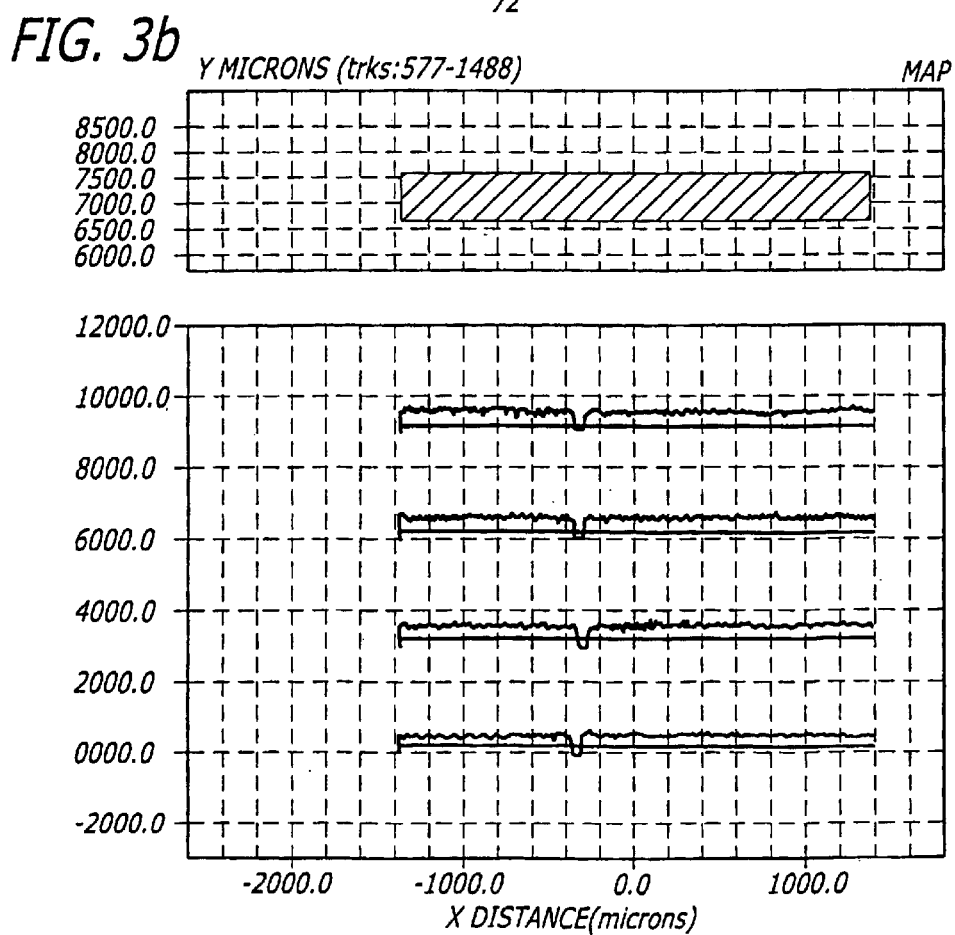
FIG. 3b aligns, in X-axis registration, an electrical response reported in the HF signal along four wobble tracks that pass through an area of the disc that includes a physical synchronization marker shown in FIG. 3a, according to this invention.

It will be further appreciated that a separate sensor need not be required. Rather, the read head of the optical disc drive can be used as a physical synchronization marker detector. As shown in FIG. 3a, physical synchronization markers 72 can be used to trigger data acquisition. These physical markers, when read by a read head, generate square pulses in the HF signal. FIG. 3b, for example, shows in X-axis registration, an electrical response reported in the HF signal along four wobble tracks that pass through an area of the disc that includes one of physical synchronization markers 72 shown in FIG. 3a, according to this invention. In this embodiment, the square pulse in the HF signal can be multiplexed in the sampling path and used as a trigger.

Also, it has been demonstrated that a disc drive with a SCSI interface can be controlled using customized software. Like with the consumer software, and as explained in the Example below, the customized software can also place the drive into a "test mode." The software then generates a test file, such as an "audio or data" test file, in "real time." An advantage of writing customized software is that, in contrast to consumer software packages (such as the software package by Adaptec, described below), a user is not constrained to conventional consumer software file structures and sizes. For example, our customized software presently generates a file structures with a frame of 2352 bytes at 75 frames per second.

Information can be embedded in the data read from the optical disc, such as the absolute and/or relative positions of the physical synchronization marker, an absolute time that the marker was read, etc. Relative tangential position can be derived, for example, by counting the number of detected markers in the data stream and then multiplying that number by the track pitch between adjacent turns of a spiral track (e.g., 1.6 microns). The absolute tangential position of sample area can be determined by measuring the distance (or equivalently the time) between two subsequent detected markers in the data stream and applying the appropriate mapping equations.

For example, if a marker in the data stream defines a radial position of 0 microns, distance D between the sample areas can be determined by the following equation:

$$D = \frac{1.2 \text{ m/s}}{\text{Sampling Rate}}$$

As set forth in the Example below, a Ricoh 6200S CD-RW drive was installed in a standard, Pentium® processor-based personal computer. The drive is sold commercially bundled with software from Adaptec (under the names Adaptec DirectCD and Adaptec Easy CD Creator) that can be used to write data to recordable optical media.

The bundled software permits the user to engage the drive's test mode to ensure that user-selected data may be written without error. In this mode, the software requests that the user specify one or more data files that are intended to be written to the recordable media; the software places the drive into test mode and sends the data to the drive. But for pulsing of the laser at levels suitable for writing, which is disabled, all drive operations are engaged, thus testing whether the data can be written to the disc without error. At the conclusion of the process, the software reports whether errors were encountered. As a concomitant of this process, however, the wobble is tracked for the entire time that data are being written. We track the wobble of a CD-R, for example, because there are no pits and lands.

Thus, as further described in the Example below, the Ricoh drive was compelled constitutively to read the wobble on assay discs by using the software to place the drive in test mode and then send appropriate "dummy" files to the drive.

Files were chosen on the basis of size—that is, chosen to ensure that the wobble is tracked long enough to read through an assay site engineered on the disc—and on the basis of prior successful use, that is, prior demonstration that they could be sent without causing the software to report buffer underrun or overrun. The process may be practiced with any data file that may be written to the drive, such as a .WAV file, a data file; a CD-ROM mode 1 image, etc. The data bear no necessary relationship to the data to be read from the analyte-specific disc; the data serve only to maintain active the drive's tracking of the disc's wobble track.

Although hijacking the drive's test mode is one approach to compelling a consumer-level optical disc drive to read the wobble without pulsing of the laser at energies required for the writing process, other strategies will no doubt become available in the future, and may be implemented in software, firmware, or drive hardware. Whatever the means, the critical observation, first made here, is that the wobble, deemed redundant by the Orange Book standard once data are written to the disc, in fact proves remarkably useful during reading.

In addition to the software-directed modification of the drive's function, two separate physical modifications were made, set forth in detail in the Example, to generate the data shown in FIGS. 6–14.

First, a lead was attached to tap the nonequalized HF output of the drive. The tapped analog HF signal was buffered, filtered, and processed with a variable gain amplifier and input to an ULTRAD-1280 dual 40 MHZ 12 bit A/D PCI data acquisition board (available from the Ultraview Corporation, of Orinda, Calif.) installed, with its own bundled software, in a second Pentium® processor-based personal computer (the "data" computer). The ULTRAD data acquisition board permits the analog signal to be sampled, digitized, and written as a bit stream to a binary file on the computer's hard disc, thereafter to be interpreted by software.

In a second modification, a photodiode was inserted into the drive in a position that permitted the diode to interrogate the edge of the disc with the marker (shown in FIGS. 1a–1b) during disc rotation. The diode signal was output to a programmable logic chip, which was connected to the triggering port of the ULTRAD-1280. Although use of a marker to acquire data is unnecessary, at a 10 MHZ sampling rate at 12 bits per data point (i.e., sample), the data storage needed to record the entire assay disc (74 minutes at 1× speed) could be unwieldy. Thus, as described in detail above, a physical synchronization marker, used as a triggering mark, was painted on the edge of the assay disc assembly at a location rotationally earlier than the assay site itself. With each rotation, the photodiode would detect the triggering mark and trigger data acquisition by the sampling card. The duration of sampling (i.e., data acquisition), controlled by software, was less than a full rotation, resulting in data files of somewhat more manageable size. As further discussed below, real-time filtering based on image-recognition algorithms that direct storage of preferred data is an alternative, and oft preferred, means of reducing data file size.

The exemplary data collected in the Example, shown in FIGS. 6–14, were obtained from a disc manufactured with a 100 nm groove depth and 1.6 µm spiral pitch, manufactured as described in Example 5 of copending and commonly owned U.S. patent application Ser. No. 09/311,329, filed May 14, 1999, to which was glued a laser-refracting non-integral polycarbonate cover manufactured as described in Example 6 of the same application. As a result of this cover, no modification of the 6200S CD-RW optical pickup was required; the cover sufficiently aided focus as to obviate the addition of further focusing the lens. It will be appreciated that physical synchronization markers could also be provided on the cover. Thus, physical synchronization markers according to this invention could be provided on one or more components of an optical disc assembly, which could include an optical disc, a cover, or a combination thereof.

Figure 5:
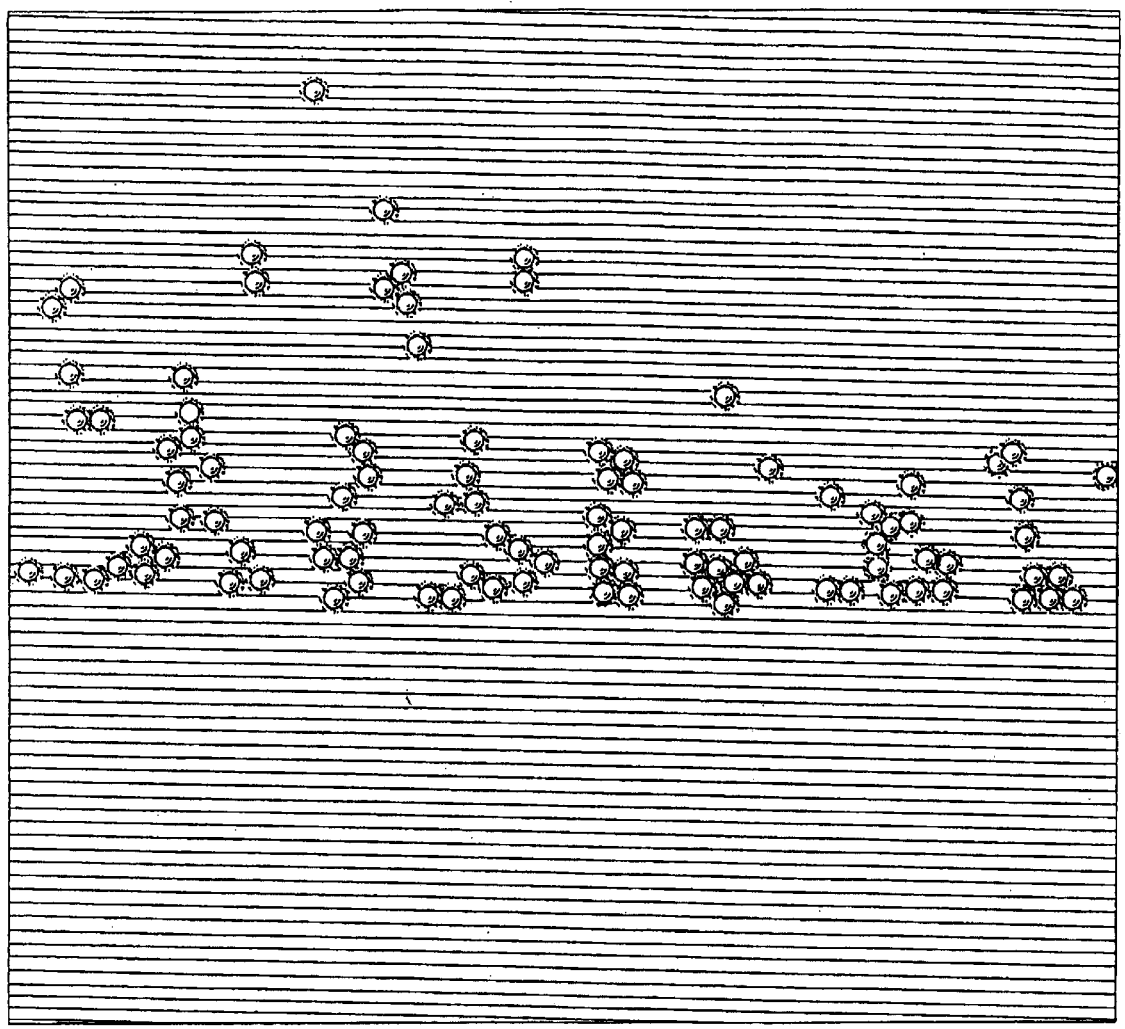
FIG. 5 shows a higher magnification of a portion of the same disc as shown in FIG. 4.
Figure 6:
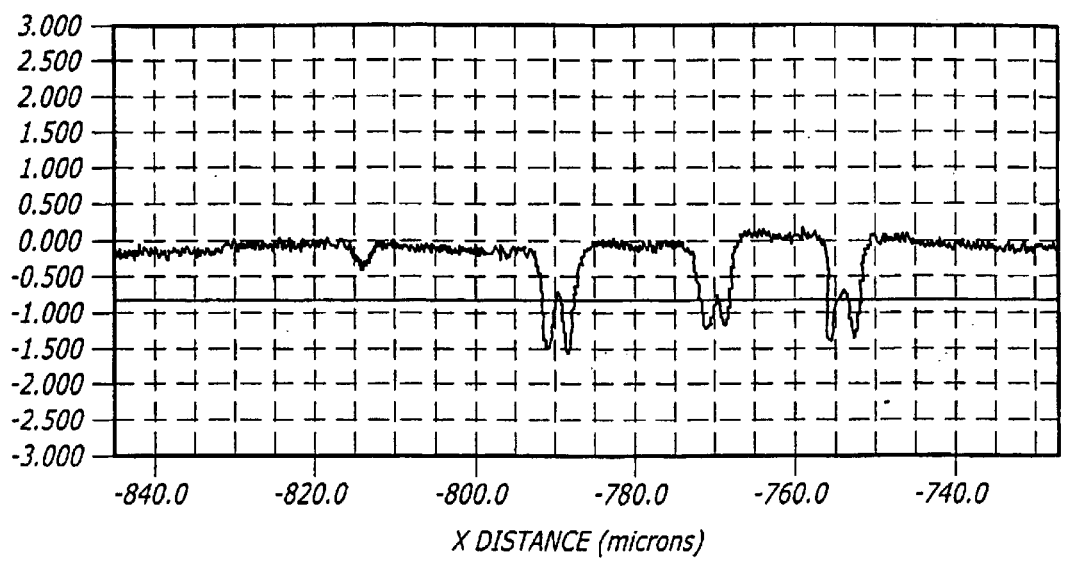
FIG. 6 shows the electrical response reported in the HF signal along a single one of the wobble track features that passes through the area of the disc shown in FIG. 5.
Figure 7:
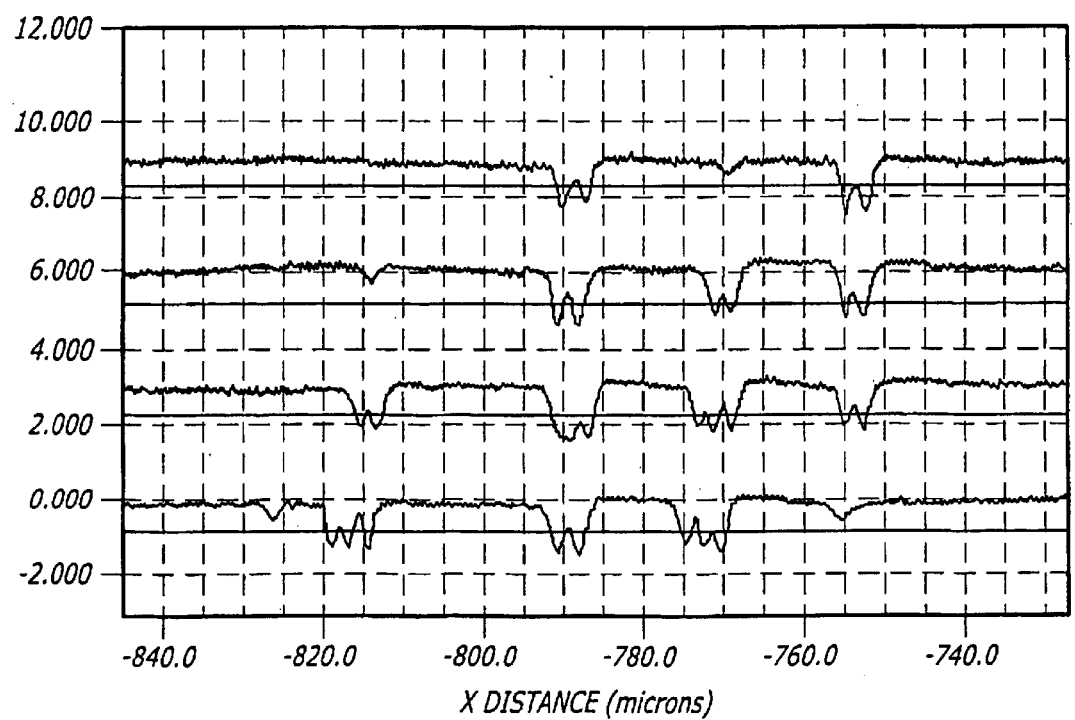
FIG. 7 aligns, in X-axis registration, the electrical response reported in the HF signal along four of the wobble tracks that pass through the area of the disc shown in FIG. 5, with the track shown in FIG. 6 appearing as the second track from the top.
Figure 8:
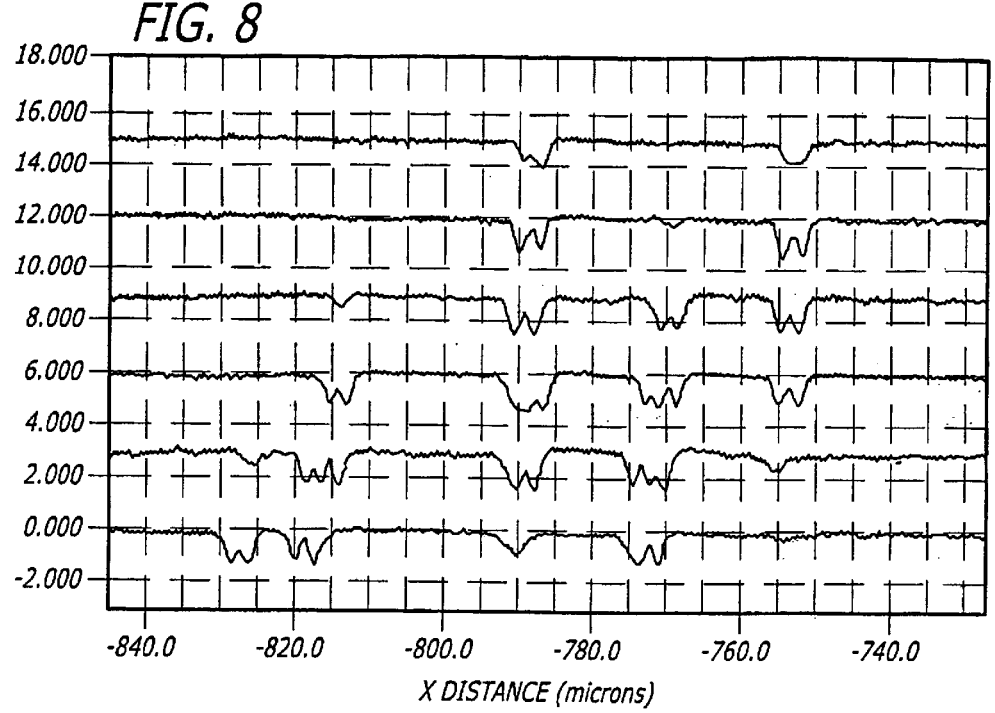
FIG. 8 aligns the electrical response reported in the HF signal along six of the wobble tracks that pass through the area of the disc shown in FIG. 5.
Figure 9:
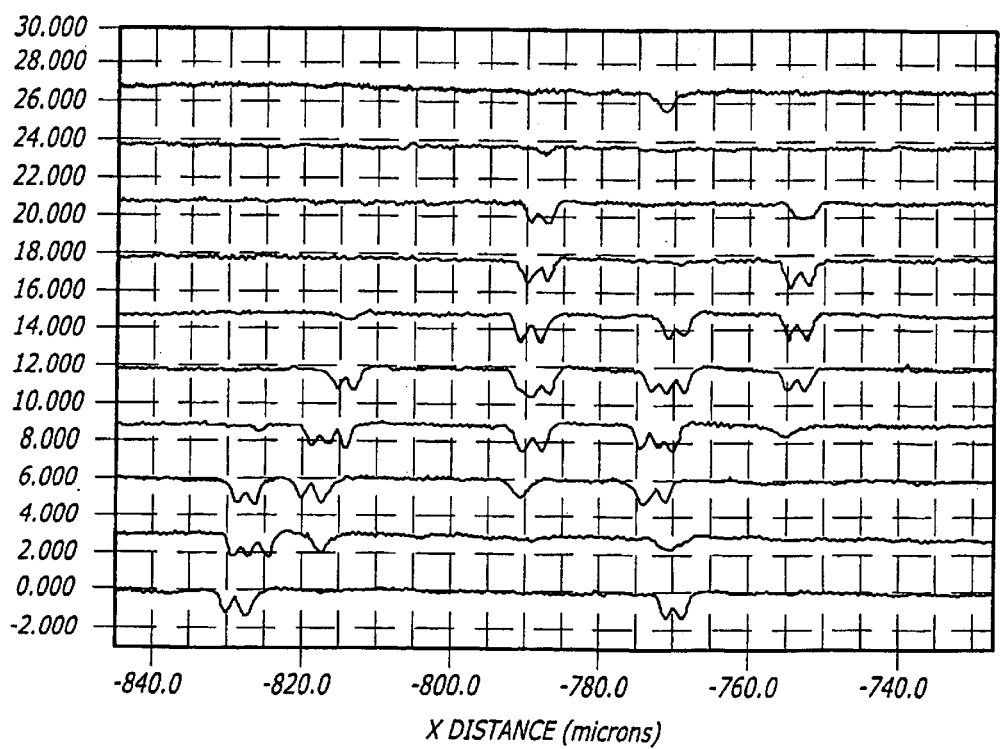
FIG. 9 aligns the electrical response reported in the HF signal along ten of the wobble tracks that pass through the area of the disc shown in FIG. 5, demonstrating that alignment of such signals permits the location of a sphere in both the X and Y dimensions to be mapped in two dimensions.

For purposes of the experiments reported in the Example, the nonoperational structures (e.g., signal elements) applied to the disc (before application of the cover) were commercially-available superparamagnetic beads uniformly 2.8 µm in diameter. The beads, suspended in water, were placed on the disc in a spot 28 mm from the disc center. The water was allowed to dry and the beads were aligned with an air gun along the direction of the track. FIG. 4 is a composite picture constructed from light microscopic images obtained during inspection of the relevant area of the disc surface after placement of the analyte-specific signal elements. Each panel is shown at 300× magnification. FIG. 5 shows one of the areas at higher magnification. At this increased magnification the track is readily observable; magnification precludes the continuity of the track from being observed.

Neither the 28 mm location nor bead alignment along the track is obligatory.

Discs are read from inner diameter to outer diameter: the wobble begins at approximately 21.7 mm, as measured from the inner diameter; data begins at 25 mm. The aliquot of microbeads was placed at 28 mm to provide the fastest route in this experiment to the data. It will be understood, however, that analyte-specific signal elements may be detected, and thus placed, anywhere within the information area of the disc.

Furthermore, the beads were manually aligned along a track simply to test the optical disc reader's ability to discriminate signal elements closely spaced along the direction of tracking. Although not wishing to be bound by any theory, the beads were believed to be adhered simply by electrostatic interaction with the disc surface. There is no obligate requirement for such spatial distribution or such noncovalent attachment: the beads may more usefully be situated by immunospecific or nucleic acid-driven adherence.

As further described in the Example, as soon as the Adaptec software indicated that the optical disc drive had begun wobble tracking (that is, had entered test mode and had ostensibly begun writing the dummy files to the disc), the Ultraview data acquisition software on the data computer was manually engaged.

With each revolution, the opaque physical synchronization marker painted on the optical disc's edge triggered data acquisition by the ULTRAD-1280 for a period less than a full rotation. The data were written as a single binary file to the hard disc drive of the "data" computer.

EXAMPLE

Analyte-Specific Signal Acquisition From a Consumer-Level Drive

A CD-R mother part was fabricated to order at CINRAM, essentially as set forth in Example 1 of copending and commonly owned U.S. patent application Ser. No. 09/311, 329, filed May 14, 1999, which is hereby incorporated by reference in its entirety, to serve directly as a stamper to produce trackable, single data-layer, forward image (i.e., inverted structure), wobbled track discs. The mother part was used to stamp about 5,000 polycarbonate discs, as set forth in Example 5 of the same patent application, which were then metalized with gold and stored for subsequent use.

One of those discs was cleaned with oxygen plasma at 75 watts for 1 minute. A 1.5 µL aliquot of streptavidin-coated Dynabeads® (2.8 µm diameter, Dynal) suspended in water at a concentration of approximately 1,000 beads/µL was placed on the disc at a spot approximately 28 mm from the center of the disc. The disc was placed on a CD chunk with imbedded magnets aligned under the spot of beads. Although the use of aligned magnets is not necessary, they may be preferable if the beads have a tendency to clump together. For a complete description of magnetic alignment techniques that can be used with this invention, see commonly owned Siddiqi et al., U.S. patent application Ser. No. 60/150,287, filed Aug. 23, 1999, and entitled Methods and Apparatus For Physical Patterning Of Nonoperational Structures On An Optical Disc, which is hereby incorporated by reference in its entirety. An air gun was then used both to align the beads in the direction of a track and to remove the water. It is believed that the beads remained adherent to the disc through noncovalent interactions with the disc surface.

A polycarbonate cover, manufactured as set forth in Example 6 of copending and commonly owed U.S. patent application Ser. No. 09/311,329, filed May 14, 1999, was attached to the disc to create a disc assembly as follows:

A plastic tray from a CD holder (sometimes referred to as a "jewel case") was used to immobilize the disc with adherent beads upwards and stacking ring facing downward. Methylethylketone ("MEK"; as sold for paint stripping at a retail hardware store) was applied with dropper to the disc's clamping ring. The cover was then placed, stacking ring upwards, on top of the disc and pressed gently against the disc for about 30 seconds. The MEK affixed the cover to the disc at the clamping ring. At the outer diameter of the assembly, the disc and cover remained closely apposed but unattached.

As described above with reference to FIG. 1, the outer edge of the disc assembly was marked manually with a physical synchronization marker (i.e., marker 5 of FIG. 1) of standard white opaque correction fluid at a spot rotationally slightly earlier (about 15 degrees earlier) than the location of the assay spot to serve as a trigger for data acquisition. It will be appreciated that the use of short distances between the marker and the assay spot reduces misalignment during mapping of the data.

A Ricoh 6200S CD-RW optical disc (a 6× speed reader/2× speed recorder) was installed in a first, standard Pentium® processor-based personal computer (the "drive" computer). The bundled software package from Adaptec was installed on the same computer.

The nonequalized HF output of the 6200S CD-RW drive was buffered, filtered, and processed with a variable gain amplifier. The signals were connected by BNC to an ULTRAD-1280 dual 40 MHZ 12 bit A/D PCT data acquisition board (available from the Ultraview Corporation, of Orinda, Calif.) installed, with its own bundled software, in a second Pentium® processor-based personal computer (the "data" computer). Additionally, a photodiode was inserted into the 6200S drive in a position that permitted the diode to interrogate the disc edge during disc rotation. The diode signal was output to the triggering port of the ULTRAD-1280. This permitted the opaque physical synchronization marker on the disc edge to signal the ULTRAD data acquisition card that the assay area was shortly to pass under the drive's optical disc pickup.

Data files were chosen on the "drive" computer of sufficient size to ensure that the drive would track the wobble track through the entire area of the disc to which beads were adherent (the assay area). The Adaptec software bundled wit the CD-RW drive was instructed to test the writing of these files to the disc. The files sent had previously been shown not to return buffer underrun, buffer overrun, or other errors.

As soon as the Adaptec software indicated that the optical disc drive had begun wobble tracking (that is, had ostensibly begun writing of data to the disc), the Ultraview data acquisition software on the data computer was manually engaged. The software directed data acquisition for a user-specified duration (e.g., b-time) following a user-defined delay (e.g., a-time) after receipt of the triggering signal.

With each revolution, the marker painted on the optical disc's edge triggered data acquisition by the ULTRAD-1280 for a period of less than a full rotation. The data were written as a single binary file to the hard disc drive of the "data" computer.

It has been further discovered since this example, that MEK may be harmful to certain biological agents. Accordingly, we now utilize an optically isotropic adhesive with a refractive index that substantially matches the refractive index of the cover. By matching the refractive indices, the light that would normally scatter at the boundary between the disc cover and air (located between the disc and the cover) is substantially eliminated. Thus, in contrast to the MEK method, which held the optical disc and the cover together near the inner diameter (tangentially inside the information area), the adhesive can be placed directly on the information area. One type of adhesive that can be used according to this invention is sold under the name DVD Bonding Adhesive, available form Targray Technology International, Inc. of Pointe-Claire, Canada.

The adhesive can be used according to the following technique. First, a thin and substantially uniform layer of the adhesive can be applied to the surface of cover (or disc) by, for example, spinning the cover (or disc). After the adhesive is applied to a surface, the cover is attached to its complementary disc to form an optical disc assembly. The assembly is then exposed to UV light to set the adhesive. For a review of DVD bonding materials, see the article by Chu Ha and Vadim Krongauz entitled "DVD Bonding Basics," *One to One Magazine*, Issue 108 (July 1999).

What is claimed is:

1. An optical disc system including an optical disc assembly having a cover with physical synchronization markers adapted to enable a counting of data points to thereby determine a radial position of a respective data point associated with said optical disc assembly, said optical disc system comprising:
    means for detecting at least one physical synchronization marker on said cover;
    means for reading data from said optical disc assembly in response to detecting said at least one physical synchronization marker on said cover; and
    means for determining possible presence of an analyte material by analyzing the data read from said optical disc assembly.

2. A method for acquiring data from an optical disc assembly including a cover having physical synchronization markers, said method comprising:
    detecting at least one physical synchronization marker on an optical disc cover;
    reading data from said optical disc assembly in response to detecting said at least one physical synchronization marker; and determining possible presence of an analyte material by analyzing the data read from said optical disc assembly.

3. A method for acquiring data from an optical disc in combination with a cover having physical synchronization markers, said method comprising:

detecting at least one physical synchronization marker on said cover;

reading data from said optical disc in response to detecting said at least one physical synchronization marker on said cover; and determining possible presence of an analyte material by analyzing the data read from said optical disc.

4. An apparatus for acquiring data from an optical disc assembly using physical synchronization markers, said apparatus comprising:

an optical disc drive capable of reading operational and nonoperational structures from an optical disc assembly; and a photodetector for detecting at least one physical synchronization marker on a cover associated with said optical disc assembly, said physical synchronization marker adapted to enable a counting of data points to thereby determine a radial position of a respective data point associated with said optical disc assembly so that possible presence of an analyte material is determined by analyzing the data read from said optical disc assembly.

5. An optical disc system, comprising:

an optical disc assembly having a cover with physical synchronization markers adapted to enable a counting of data points to determine a radial position of a respective data point associated with said optical disc assembly;

a detector implemented to detect at least one physical synchronization marker on said cover of said optical disc assembly; and a reader that reads data from said optical disc assembly in response to detecting said at least one physical synchronization marker on said cover to thereby determine possible presence of an analyte material by analyzing the data read from said optical disc assembly.

* * * * *